(12) United States Patent
Madhavan et al.

(10) Patent No.: US 8,322,196 B2
(45) Date of Patent: Dec. 4, 2012

(54) VIBRATING WIRE VISCOMETERS

(75) Inventors: Raghu Madhavan, Yokohama (JP); Yu Hatori, Tokyo (JP); Mami Nishida, Sagamihara (JP); Sophie Nazik Godefroy, Cairo (EG); Michael Stangeland, Tokyo (JP); Go Fujisawa, Sagamihara (JP)

(73) Assignee: Schlumberger Technology Corporation, Sugar Land, TX (US)

( * ) Notice: Subject to any disclaimer, the term of this patent is extended or adjusted under 35 U.S.C. 154(b) by 605 days.

(21) Appl. No.: 12/534,151

(22) Filed: Aug. 2, 2009

(65) Prior Publication Data
US 2011/0023587 A1 Feb. 3, 2011

(51) Int. Cl.
*G01N 11/10* (2006.01)
(52) U.S. Cl. ...... 73/54.41; 73/54.02; 73/54.24; 73/54.26; 73/152.28; 73/152.32; 73/152.47; 73/861.12
(58) Field of Classification Search ............ 73/54.02, 73/54.14, 54.23–54.27, 54.41, 152.28, 152.32, 73/152.47
See application file for complete search history.

(56) References Cited

U.S. PATENT DOCUMENTS

| 4,860,581 | A | 8/1989 | Zimmerman et al. |
| 4,936,139 | A | 6/1990 | Zimmerman et al. |
| 5,526,698 | A | * | 6/1996 | Sakurai et al. ............. 73/861.12 |
| 7,194,902 | B1 | 3/2007 | Goodwin |
| 7,222,671 | B2 | * | 5/2007 | Caudwell et al. .......... 166/252.5 |
| 7,574,898 | B2 | * | 8/2009 | Harrison et al. ............ 73/54.41 |
| 8,166,812 | B2 | * | 5/2012 | Desroques et al. ........ 73/152.28 |

FOREIGN PATENT DOCUMENTS

| GB | 2456034 | 7/2009 |
| JP | 5034257 | 2/1993 |
| WO | 2009/061563 | 5/2009 |

* cited by examiner

*Primary Examiner* — Hezron E Williams
*Assistant Examiner* — Hoang Nguyen
(74) *Attorney, Agent, or Firm* — Jianguang Du; Jody DeStefanis

(57) ABSTRACT

Vibrating wire viscometers are described. Some example vibrating wire viscometer housings include a flowline through the housing to expose a first wire to a downhole fluid, a cavity in the housing to hold a magnet and to conduct one or more additional wires from the flowline to a signal generator, first and second electrically conductive posts mechanically coupled to the housing to hold the first wire in tension within the flowline, and a seal mechanically coupled to the housing to prevent access to the magnet by the downhole fluid.

18 Claims, 12 Drawing Sheets

VIBRATING WIRE VISCOMETERS

FIELD OF THE DISCLOSURE

This disclosure relates generally to testing viscosity of downhole fluids and, more particularly, to vibrating wire viscometers.

BACKGROUND

In the field of downhole petroleum and natural gas exploration, fluid property measurement under native or in situ conditions is an important tool to surveyors to understand the economic viability of a subterranean formation. Among the fluid properties of interest is viscosity. However, the downhole environments in which such fluid properties are determined may cause problems for the tools used to collect data. For example, the heat, shock, pressure, and vibration present in the downhole environment may cause deterioration of the tools and/or loss of measurement accuracy.

SUMMARY

Vibrating wire viscometers are disclosed herein. In some described examples, a vibrating wire viscometer housing includes a flowline through the housing to expose a first wire to a downhole fluid, a cavity in the housing to hold a magnet and to conduct one or more additional wires from the flowline to a signal generator, first and second electrically conductive posts mechanically coupled to the housing to hold the first wire in tension within the flowline, and a seal mechanically coupled to the housing to prevent access to the magnet by the downhole fluid.

In some additional examples, a vibrating wire viscometer includes a signal generator and a housing. The example housing includes a first flowline and a cavity fluidly coupled to the first flowline, wherein a removable sensor block is inserted into the cavity. The example removable sensor block includes a second flowline which, when inserted into the cavity, substantially aligns with the first flowline, a magnet to generate a magnetic field across the flowline, first and second conductive posts to hold an electrically conductive wire within the second flowline, and first and second signal wires to electrically couple respective ones of the first and second conductive posts to the signal generator.

Some additional example vibrating wire viscometers include a metallic housing having a cavity and a flowline fluidly decoupled from the cavity, first and second electrically conductive posts electrically insulated from the metallic housing and extending from the cavity to the flowline, an electrically conductive wire held in tension between the first and second electrically conductive posts to vibrate in response to an electrical signal, a magnet in the cavity and extending parallel to the conductive wire, an analyzer electrically coupled to the first and second electrically conductive posts via at least the cavity to determine a viscosity based on the vibration of the electrically conductive wire, and an encapsulation material to fill the cavity to fluidly decouple the cavity from the flowline and from a downhole fluid surrounding the metallic housing.

In some other examples, a vibrating wire viscometer includes a housing having a flowline to allow a downhole fluid to flow through the flowline, a wire to vibrate in the flowline in response to an alternating current, a cover coupled to the housing, first and second electrically conductive posts to hold the wire in tension in the flowline, wherein the first and second electrically conductive posts are hermetically sealed between the housing and the cover, and an analyzer electrically coupled to the first and second electrically conductive posts to measure a reverse voltage on the wire to determine a viscosity of the downhole fluid.

DETAILED DESCRIPTION

Figure 2:
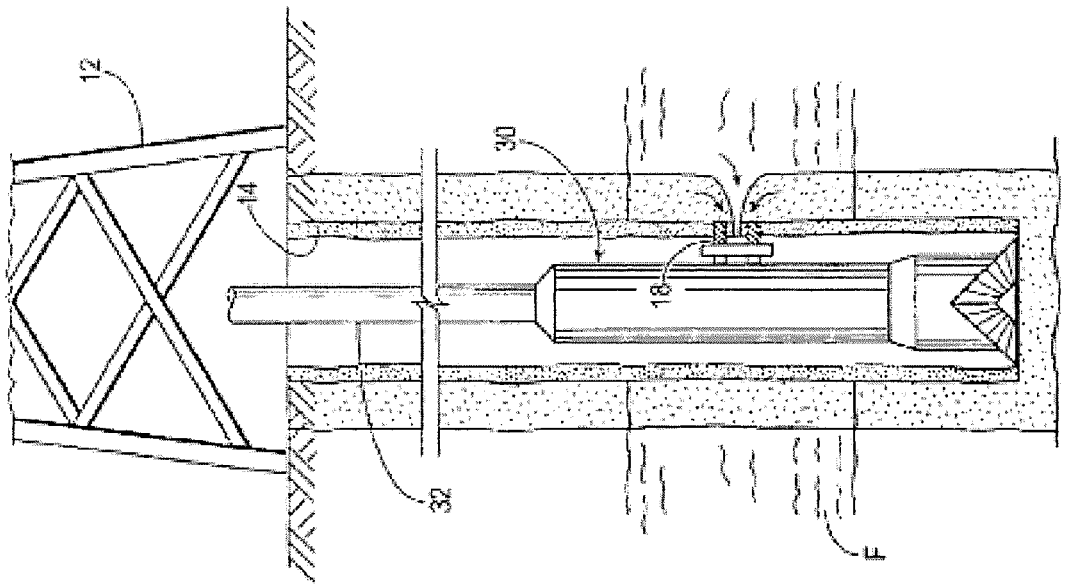
FIG. 2 depicts a drilling tool that may employ the example viscometers described herein.

Certain examples are shown in the above-identified figures and described in detail below. In describing these examples, like or identical reference numbers are used to identify common or similar elements. The figures are not necessarily to scale and certain features and certain views of the figures may be shown exaggerated in scale or in schematic for clarity and/or conciseness. Accordingly, while the following describes example systems, persons of ordinary skill in the art will readily appreciate that the examples are not the only way to implement such systems.

Different aspects and/or features of the example vibrating wire viscometers are described herein. Many of these different aspects and/or features may be combined to realize the respective advantages of these aspects and/or features. Different applications and implementations of the vibrating wire viscometers described herein may benefit from some combination of the below-described features compared to other combinations.

The example vibrating wire viscometers described herein may be used to measure the viscosity of a downhole fluid during a subterranean fluid sampling and/or analysis operation. In some applications, the viscometers are at least partially immersed in downhole fluid, which can be corrosive or damaging to some equipment, particularly electrical devices such as sensors and the like. Therefore, some example vibrating wire viscometers described herein include a metallic housing having a flowline and two slots. The metallic housing and the vibrating wire may be small to improve the space efficiency of a downhole tool. A flowline may allow downhole fluid to flow through the example viscometers, and a conductive wire may be disposed within the flowline. In some examples, the conductive wire is held in tension between two conductive posts, which traverse the flowline between the two slots and which are electrically decoupled or insulated from the metallic body. In some additional examples, the slots may hold one or more permanent magnets in parallel with the flowline and the tensioned electrically conductive wire to produce a magnetic field transverse to the wire. In some other examples, the magnets may be implemented using one or more electromagnets. The electromagnets may be disposed on either or both sides of the flowline to generate a magnetic field.

The example electrically conductive wire may then be subjected to an alternating current to cause the wire to vibrate at a resonant frequency within the magnetic field. The example conductive wire vibrates within the fluid, which damps the vibration of the wire by an amount that depends on the viscosity of the fluid. An analyzer circuit may then determine the viscosity of the downhole fluid by determining the amount of damping.

In some examples, the slots include electrical connections to another portion of the metallic viscometer housing. The example metallic housing may include signal generation, measurement, analysis, and/or communication devices to send and receive signals to/from outside the metallic housing. In some examples, the slots are filled with a non-conductive encapsulation material such as an epoxy, plastic, or rubber-molding. The encapsulation material may seal the slots and the components contained therein from downhole fluid(s). In some examples, the encapsulation material may transfer fluid pressure to the flowline to pressure balance the flowline relative to the downhole fluid(s) surrounding the viscometer.

In some other examples, the slots may be further sealed from the downhole fluid via a metallic cap. In such examples, the metallic cap is flexible to allow the downhole fluid to apply fluid pressure to the encapsulation material contained within the slots, thereby pressure balancing the flowline.

In some other examples, a viscometer housing is provided with a removable sensor block. Some example removable sensor blocks include a flowline to align with flowlines in the viscometer housing, one or more magnets, a wire to vibrate within the flowline, and external wires to be electrically coupled to electronic components within the housing. After an example removable sensor block is inserted into the viscometer housing, a cap may be installed to protect the removable sensor block.

In yet some other examples, the housing includes a flowline and a vibrating wire held in tension within the flowline. An example cap is then installed, where the cap includes one or more magnets mechanically attached to the cap and installed simultaneously with the cap. When installed, the magnets generate a magnetic field across the vibrating wire.

In still some other examples, a flowline may be inserted into a housing. The flowline and the housing may be sealed to prevent downhole fluid from accessing components within the housing.

Figure 1:
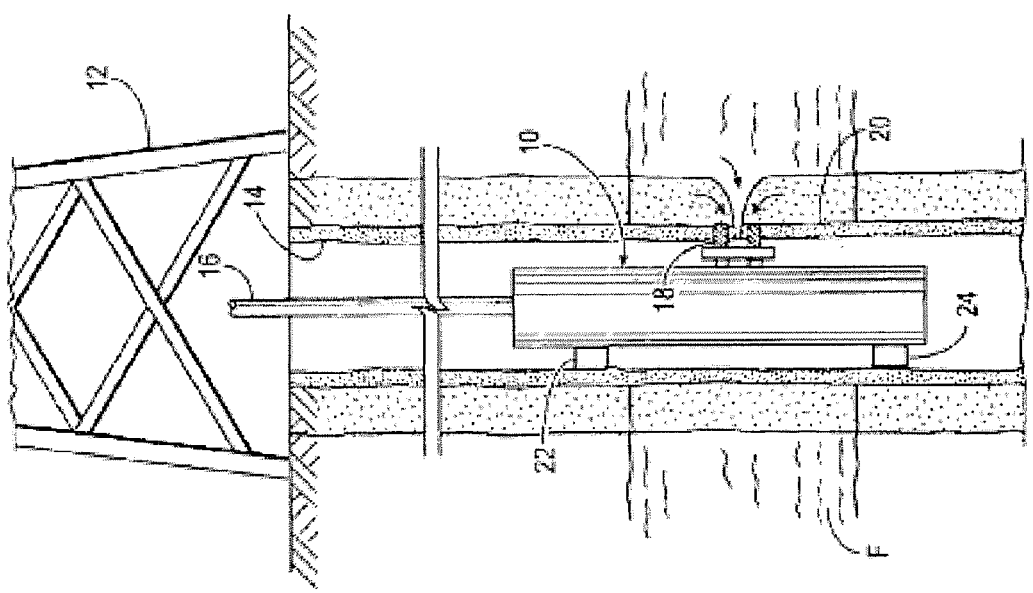
FIG. 1 depicts a wireline tool that is suspended from a rig into a wellbore and which may employ the example viscometers described herein.

FIG. 1 depicts a downhole tool 10, which is suspended from a rig 12 in a wellbore 14 and which may employ the example viscometers described herein. The downhole tool 10 can be any type of tool capable of performing formation evaluation and may be conveyed by wireline, drillstring, coiled tubing, or slickline. The downhole tool 10 of FIG. 1 is a conventional wireline tool deployed from the rig 12 in the wellbore 14 via a wireline cable 16 and positioned adjacent to a formation F. The downhole tool 10 is provided with a probe 18 adapted to seal against a wall 20 of the wellbore 14 (hereinafter referred to as a "wall 20" or "wellbore wall 20") and draw fluid from the formation F into the downhole tool 10 as depicted by the arrows. Backup pistons 22 and 24 assist in pushing the probe 18 of the downhole tool 10 against the wellbore wall 20. Additionally or alternatively, other types of sealing devices, such as dual packers, may be used to channel formation fluid into the downhole tool 10 as described in U.S. Pat. No. 4,860,581.

FIG. 2 depicts another downhole tool 30 constructed in accordance with the present invention. The downhole tool 30 of FIG. 2 is a drilling tool, which can be conveyed among one or more (or itself may be) a measurement-while-drilling (MWD) drilling tool, a logging-while-drilling (LWD) drilling tool, or other drilling tool known to those skilled in the art. The downhole tool 30 is attached to a drillstring 32 driven by the rig 12 to form the wellbore 14. The downhole tool 30 includes the probe 18 adapted to seal against the wall 20 of the wellbore 14 to draw fluid from the formation F into the downhole tool 30 as depicted by the arrows.

Figure 3:
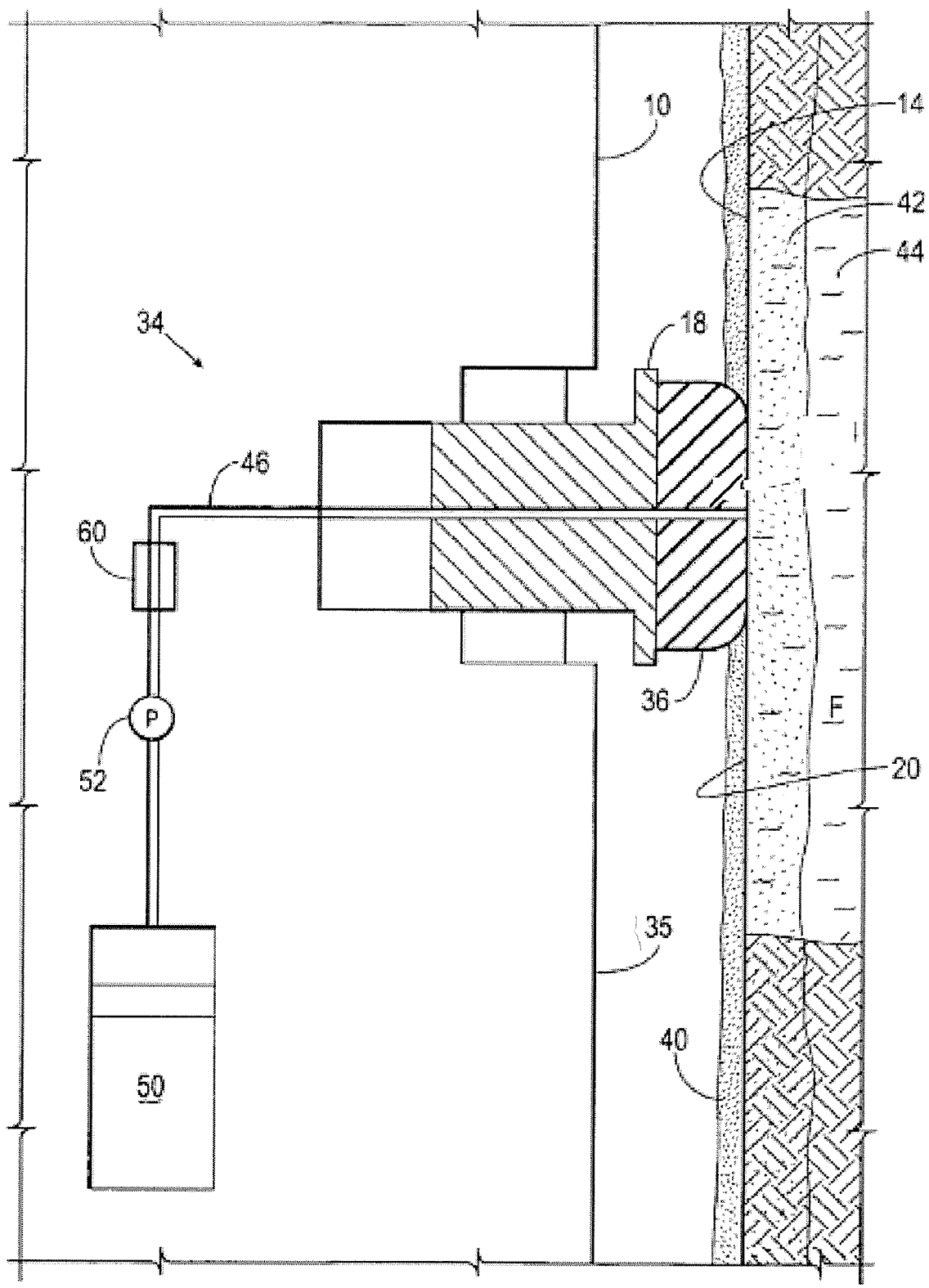
FIG. 3 is a schematic view of a portion of the downhole tool of FIG. 1 depicting a fluid sampling system.

FIG. 3 is a schematic view of a portion of the downhole tool 10 of FIG. 1 depicting a fluid sampling system 34. The probe 18 is preferably extended from a housing 35 of the downhole tool 10 for engagement with the wellbore wall 20. The probe 18 is provided with a packer 36 for sealing against the wellbore wall 20. The packer 36 contacts the wellbore wall 20 and forms a seal with a mud cake 40 lining the wellbore 14. Portions of the mud seep into the wellbore wall 20 and create an invaded zone 42 about the wellbore 14. The invaded zone 42 contains mud and other wellbore fluids that contaminate the surrounding formations, including the formation F and a portion of the virgin fluid 44 contained therein.

The probe 18 is preferably provided with an evaluation flowline 46. Examples of fluid communication devices, such as probes and dual packers, used for drawing fluid into a flowline are depicted in U.S. Pat. Nos. 4,860,581 and 4,936,139.

The evaluation flowline 46 extends into the downhole tool 10 and is used to pass fluid, such as virgin fluid 44 into the downhole tool 10 for testing and/or sampling. The evaluation flowline 46 extends to a sample chamber 50 for collecting samples of the virgin fluid 44 or may be redirected to discard the sample. A pump 52 may be used to draw fluid through the flowline 46.

While FIG. 3 shows a sample configuration of a downhole tool used to draw fluid from a formation, it will be appreciated by one of skill in the art that a variety of configurations of probes, flowlines and downhole tools may be used and is not intended to limit the scope of the invention.

In accordance with the present invention, a viscometer 60 is associated with an evaluation cavity within the downhole tool 10, such as the evaluation flowline 46 for measuring the viscosity of the fluid within the evaluation cavity. Example implementations of the viscometer 60 are shown in more detail in connection with FIGS. 4-19.

The downhole tool 30 may also be provided with the housing 35, the probe 18, the fluid flow system 34, the packer 36, the evaluation flowline 46, the sample chamber 50, the pump(s) 52 and the viscometer(s) 60 in a similar manner as the downhole tool 10.

Figure 4:
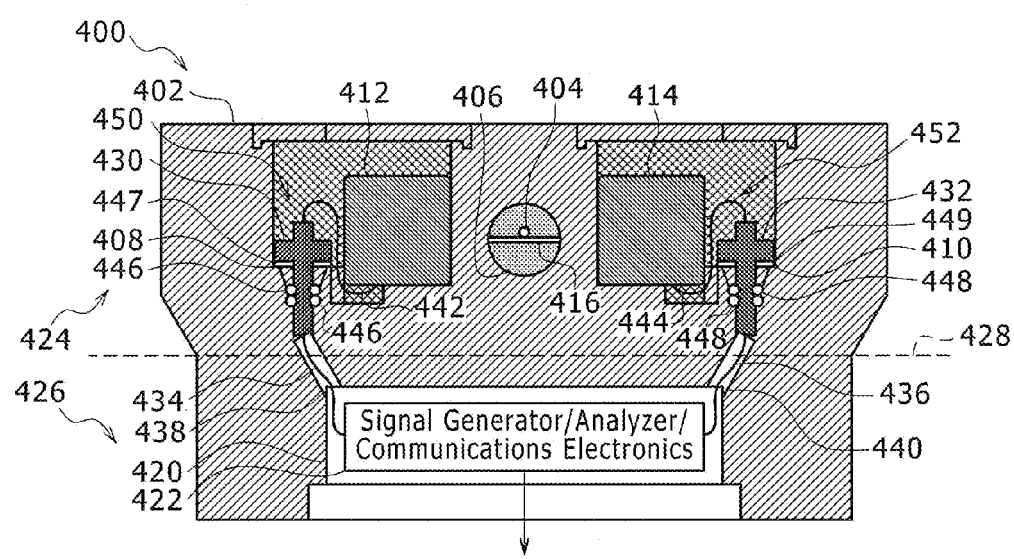
FIG. 4 is a cross-sectional view of an example vibrating wire viscometer with encapsulation sealing.
Figure 5:
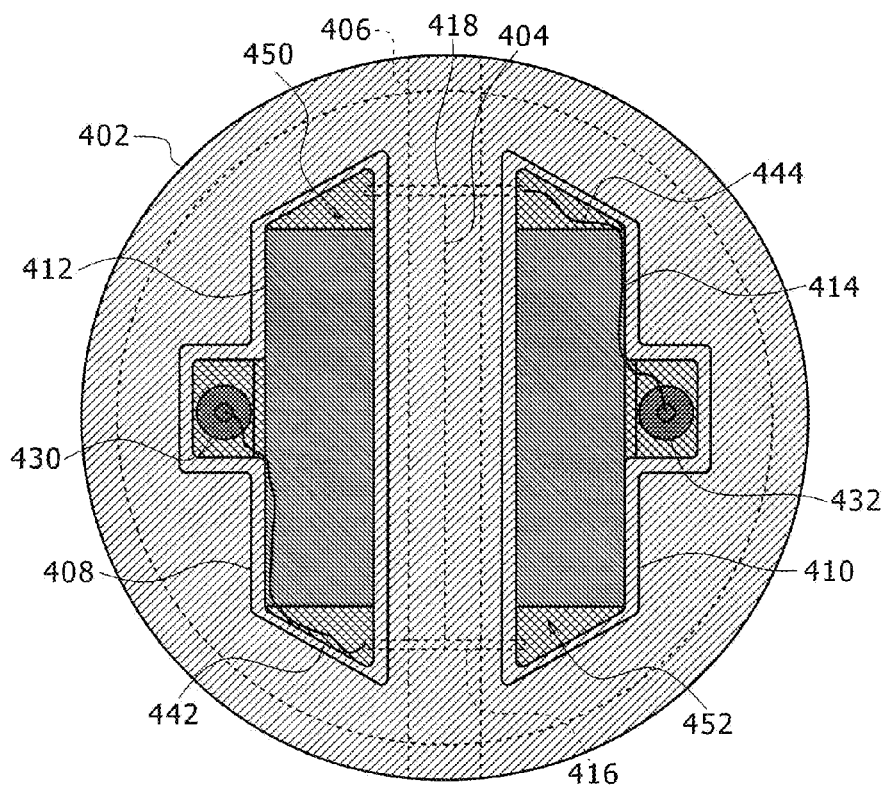
FIG. 5 is a plan view of the example vibrating wire viscometer of FIG. 4.

FIG. 4 is a cross-sectional view of an example vibrating wire viscometer 400 with encapsulation sealing. FIG. 5 is a plan view of the example vibrating wire viscometer 400 of FIG. 4. The example vibrating wire viscometer 400 may be used to implement the example viscometer(s) 60 described in connection with FIG. 3 to measure a viscosity of a downhole fluid.

The example vibrating wire viscometer 400 includes a housing 402 to expose a wire 404 to a downhole fluid. The example housing 402 is made of a metal such as steel, aluminum, Densimet® D176 (a tungsten alloy) or another strong, relatively inert metal. To expose the wire 404 to downhole fluid during, for example, a downhole sampling and/or analysis operation, the housing 402 includes a flowline 406 through which downhole fluid may flow. The downhole fluid may access the flowline 406 via a sampling line fluidly coupled to the flowline 406 and/or by at least partially immersing the housing 402 within the downhole fluid. In some examples, the wire 404 is implemented using tungsten.

Figure 18:
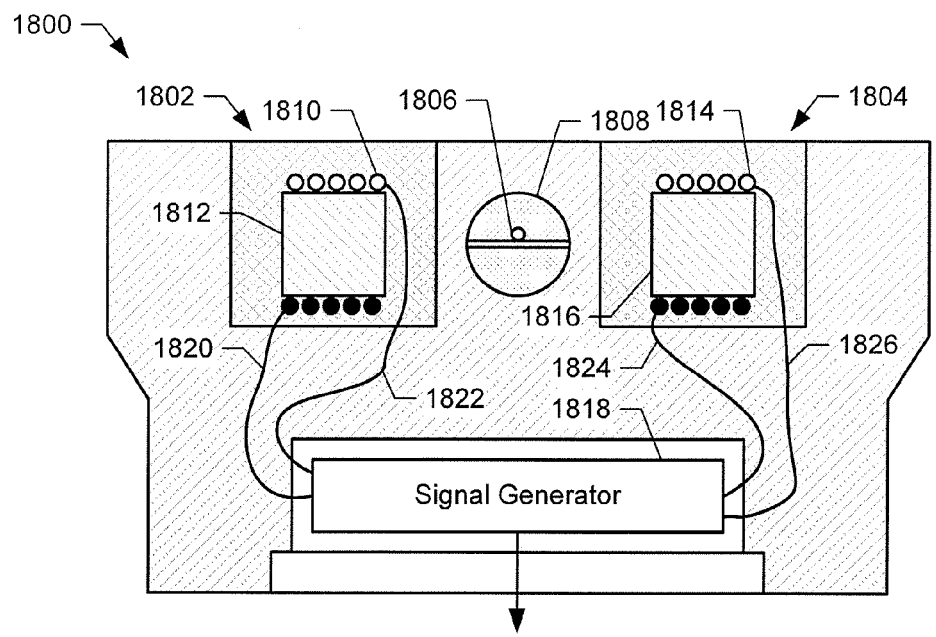
FIG. 18 is a schematic diagram of an example vibrating wire viscometer configuration including electromagnets.

The example housing 402 further includes two cavities or slots 408 and 410, in which magnets 412 and 414 are placed. The magnets 412 and 414 generate a magnetic field across the wire 404. In some examples, the magnets 412 and 414 are permanent magnets. In some other examples, the magnets 412 and 414 are implemented using one or more electromagnets as illustrated in FIG. 18 below. As illustrated in FIG. 5, the magnets 412 and 414 are located within respective ones of the slots 408 and 410, and generate a magnetic field in the flowline 406 (i.e., across the wire 404).

To support the wire 404 within the flowline 406, the example vibrating wire viscometer 400 further includes two posts 416 and 418. As illustrated in FIG. 5, the posts 416 and 418 are located between the slots 408 and 410 near the ends of the flowline 406. The example posts 416 and 418 are electrically coupled to the wire 404 to deliver alternating current to the wire 404. The posts 416 and 418 further provide mechanical support to hold the wire 404 in a substantially constant tension within the downhole fluid. The length and tension of the wire 404 directly affect the resonance frequency, and therefore should be held constant to achieve accurate measurements. In the illustrated example, the wire 404 is fastened to the posts 416 and 418 via laser welding. The posts 416 and 418 are mechanically coupled to the housing 402 within the flowline 406 and between the slots 408 and 410. However, the posts 416 and 418 are electrically decoupled or insulated from the housing 402 to avoid short-circuiting the wire 404. In some examples where the downhole fluid is highly corrosive, the posts 416 and 418 are implemented using Inconel® and/or Hastelloy®. In examples where the downhole fluid is less corrosive, the posts 416 and 418 may instead be implemented using Kovar®.

The example housing 402 further includes a cavity 420 in which electronics 422 are disposed. The electronics 422 may be configured to cause the wire 404 to vibrate (e.g., a signal generator), to measure the viscosity of the downhole fluid via the wire 404 (e.g., an analyzer), and/or to communicate with additional tools along a drillstring or wireline tool (e.g., communications). The example cavity 420 protects the electronics 422 from downhole fluid and pressure via the housing 402. In some example applications, the vibrating wire viscometer 400 is mounted on a fluid sampling and/or analysis tool and conveyed via wireline, drillstring, coiled tubing, and/or slickline such that a first portion 424 of the vibrating wire viscometer 400 is exposed to the downhole fluids, while a second portion 426 is protected within the tool. A dashed line 428 is shown to illustrate an example wall of a sampling and/or analysis tool in which the vibrating wire viscometer 400 may be installed such that the second portion 426 is disposed within the tool.

To couple the other electronic components of the viscometer 400 to the electronics 422, the example slots 408 and 410 further include respective sealed posts 430 and 432. The sealed posts 430 and 432 are electrically coupled to the electronics 422 via respective wires 434 and 436 and passages 438 and 440. Additionally, the sealed posts 430 and 432 are each coupled to one of the posts 416 and 418 via wires 442 and 444 to electrically couple the electronics 422 to the wire 404. The example sealed posts 430 and 432 are implemented using a BeCu (beryllium copper) alloy. To seal the cavity 420 and the electronics 422 from the slots 408 and 410, seats 446 and 448 and washers 447 and 449 may be installed between the sealed posts 430 and 432 and the respective passages 438 and 440. The example seals 446 and 448 are implemented using double o-rings, because some potting materials 450 and 452 may bond to the outside o-ring and prevent proper sealing. Additionally, the washers 447 and 449 may be implemented using, for example, Kapton® to insulate the posts 430 and 432 from the housing 402.

After the example vibrating wire viscometer 400 has been assembled, the remaining space within the slots 408 and 410 is filled with an encapsulation or potting material 450 and 452 such as an epoxy, rubber, plastic, or any other suitable encapsulation material. In some examples, an epoxy may be used to implement the potting material 450 and 452, and a molding (e.g., Viton®) is used to protect the potting material 450 and 452 from the downhole fluid.

To measure the viscosity of a downhole fluid within the flowline 406, the electronics 422 (e.g., a signal generator) generate a sinusoidal or other signal at a predetermined frequency. The signal travels from the electronics 422 to the wires 434 and 442. The wire 442 is electrically coupled to the post 416, which conducts the signal to the wire 404 and to the other post 418. The post 418 is electrically coupled to the wire 444, which is further coupled to the electronics 422 via the wire 436. Thus, the electronics 422 may apply an alternating current to the wire 404. At a particular frequency, based on the length and tension of the wire 404, the wire 404 vibrates at a resonant frequency within the magnetic field provided by the magnets 412 and 414.

Based on the viscosity of the downhole fluid surrounding the wire 404, the vibration of the wire 404 may be damped and/or additional power may be required to continue to vibrate the wire 404 at the resonant frequency. The closer the magnet(s) are to the vibrating wire 404, the stronger the magnetic field will be and the stronger the amplitude of the vibration of the wire 404. A reverse voltage is generated as a result of the vibrating wire 404 and the magnetic field (e.g., a back electromotive force (emf)). The reverse voltage may be measured by the electronics 422 (e.g., an analyzer) to determine the viscosity of the downhole fluid. A further explanation of the use of a vibrating wire method to determine the viscosity of a fluid may be found in U.S. Pat. No. 7,222,671.

Figure 6:
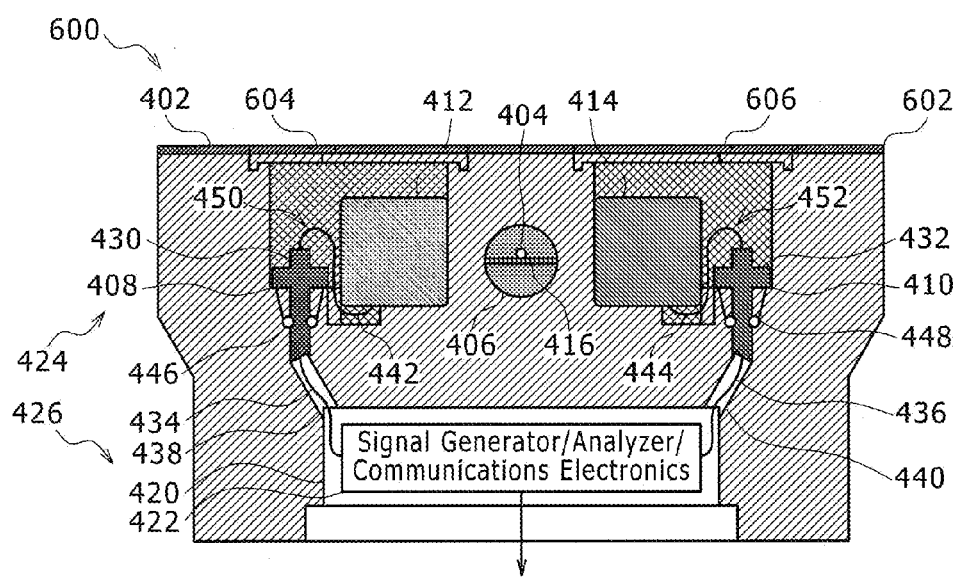
FIG. 6 is a cross-sectional view of an example vibrating wire viscometer with a flexible metallic cover seal.

FIG. 6 is a cross-sectional view of an example vibrating wire viscometer 600 with a flexible metallic cover seal 602. The example vibrating wire viscometer 600 includes the components 402-422 and 428-448 similar or identical to those used in the example vibrating wire viscometer 400 described in connection with FIG. 4. Additionally, the example slots 408 and 410 are filled with the encapsulation or potting material 450 and 452.

In contrast to the vibrating wire viscometer 400 of FIG. 4, the encapsulation material 450 and 452 is not exposed to downhole fluid surrounding the housing 402. Instead, the vibrating wire viscometer 600 includes the flexible metallic cover 602 fastened to the housing 402. The cover 602 prevents air absorption and/or other reactions between the downhole fluid and the encapsulation material 450 and 452. Additionally, the example metallic cover 602 is flexible to allow the downhole fluid to apply fluid pressure to the encapsulation material 450 and 452. The fluid pressure applied to the encapsulation material 450 and 452 is further applied to the flowline 406 as described in connection with FIG. 4 to balance the fluid pressure exerted by the downhole fluid from within the flowline 406. The metallic cover 602 may be implemented using a material such as Inconel® 718, the numeral 718 referring in this instance to a particular material commercially available under the Inconel brand and not a part of any of the drawings.

To fasten the cover 602 to the housing 402, the cover 602 may be attached by welding, brazing, and/or using any other method to attach and seal the cover 602 to the housing 402. The cover 602 may be provided with fill holes 604 and 606, through which the slots 408 and 410 may be filled with the encapsulation material 450 and 452. When the slots 408 and 410 have been filled, the holes 604 and 606 may be filled or sealed to prevent access to the encapsulation material 450 and 452 by downhole fluid.

Figure 7:
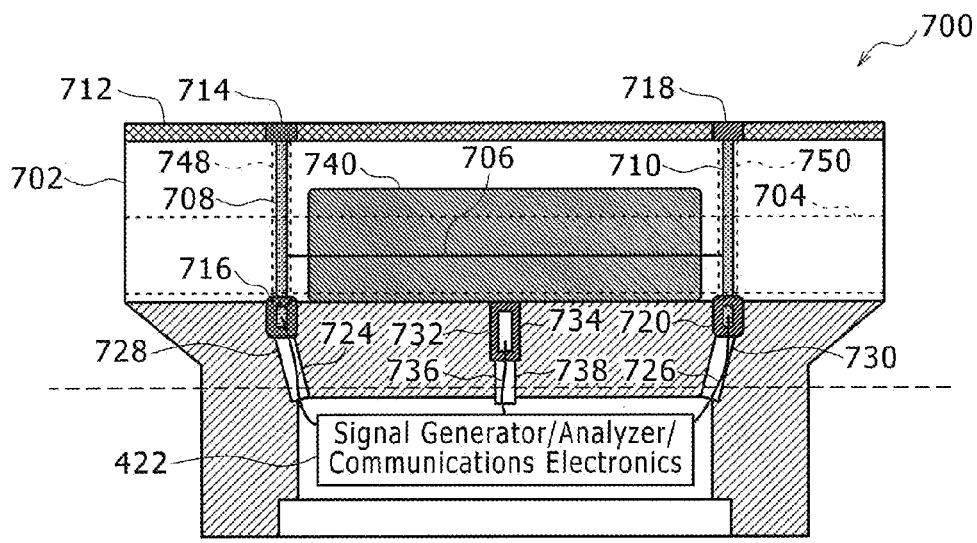
FIG. 7 is a cross-sectional view of an example vibrating wire viscometer with hermetically sealed posts.
Figure 8:
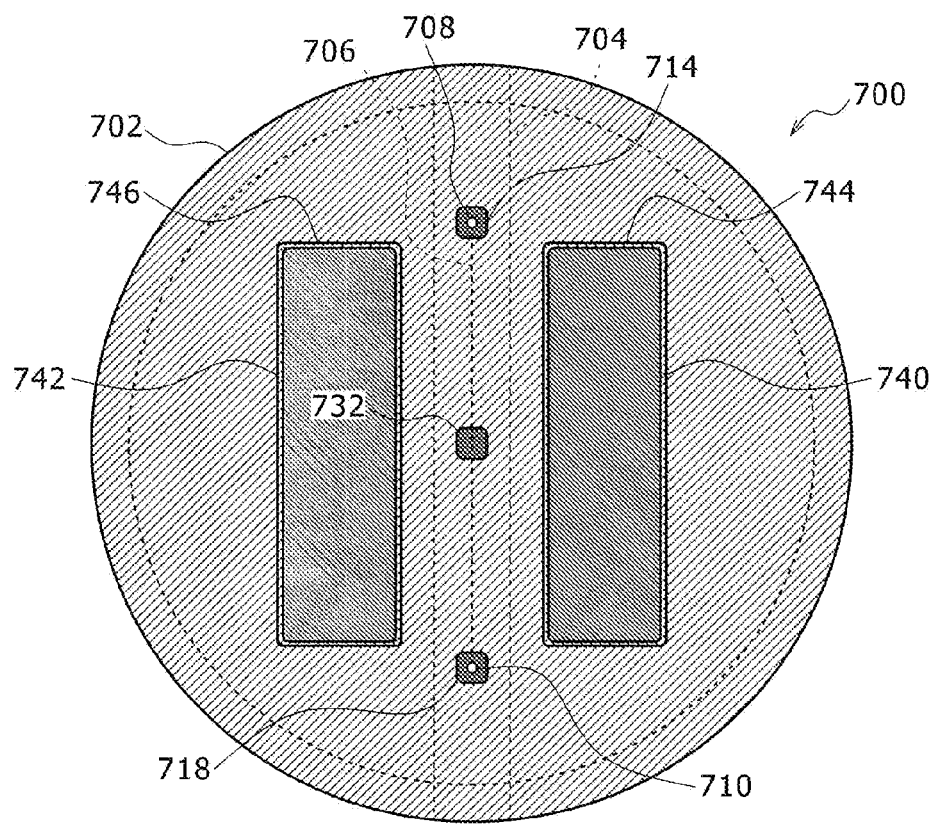
FIG. 8 is a plan view of the example vibrating wire viscometer of FIG. 7.

FIG. 7 is a cross-sectional view of an example vibrating wire viscometer 700 with hermetically-sealed posts 708 and 710. FIG. 8 is a plan view of the example vibrating wire viscometer 700. The example vibrating wire viscometer 700 includes a metallic housing 702 that includes a flowline 704. The flowline 704 allows downhole fluid to flow during, for example, a downhole fluid sampling and/or analysis operation to determine the viscosity of the downhole fluid. To determine the viscosity, the vibrating wire viscometer 700 further includes a wire 706 held in tension between the two electrically conductive posts 708 and 710.

The posts 708 and 710 are mechanically coupled or fastened between the housing 702 and a cover 712 using non-conductive hermetic seals 714, 716, 718, and 720. The hermetic seals 714-720 may be implemented using, for example, glass, ceramic, and/or any other non-conductive material to prevent the posts 708 and 710 from making electrical contact with the housing 702 and/or the cover 710.

The posts 708 and 710 may then be electrically coupled to the electronics 422. The electronics 422 may include a signal generator, an analyzer, communication devices, and/or other electronic components to determine the viscosity of the downhole fluid and/or communicate with other portions of a downhole tool. The example electronics 422 are electrically coupled to the posts 708 and 710 via wires 724 and 726 running through passages 728 and 730 in the housing 702. The passages 728 and 730 are sealed from downhole fluid by the hermetic seals 716 and 720. As a result, the posts 708 and 710 may be easier to install and couple to the electronics 422 than the example posts 416 and 418 illustrated in FIGS. 4-6.

The example vibrating wire viscometer 700 may further include a temperature sensor 732 to determine the temperature of the downhole fluid. The temperature sensor 732 is mechanically coupled to the housing 702 by a hermetic seal 734 and electrically coupled to the electronic components 422 by a wire 736 running through a passage 738. The passage 738 is sealed from the downhole fluid by the hermetic seal 734.

The vibrating wire viscometer 700 further includes magnets 740 and 742. In the view shown in FIG. 7, the magnet 742 is obscured by the magnet 740 and is not shown. The magnets 740 and 742 are both shown in the plan view illustrated in FIG. 8.

In the view illustrated in FIG. 8, the example hermetic seals 716 and 720 are obscured by the hermetic seals 714 and 718, respectively. As shown in FIG. 8, the flowline 704 allows downhole fluid to flow through the housing 702. The wire 706 and the posts 708 and 710 preferably do not interfere with the flow of the downhole fluid.

Like the magnets 412 and 414 illustrated in FIGS. 4-6, the magnets 740 and 742 may be inserted into slots or cavities 744 and 746 in the housing 702. However, the cavities 744 and 746 may be smaller than the example cavities 408 and 410 of FIGS. 4-6 because the sealed posts 430 and 432 are not needed to route the wires 724 and 726 to the electronics 422. In fact, the example cavities 744 and 746 may be made to precisely fit the magnets 740 and 742. In some examples, the remainder of the cavities 744 and 746 may be filled with an encapsulation material such as the encapsulation material 450 and 452 described in connection with FIGS. 4-6. As described above, the encapsulation material may be used in combination with the flexible cover 712 to balance the fluid pressure exerted on the housing 702 from within the flowline 704.

To install the example wire 706 and the posts 708 and 710 into the housing 702, the cover 712 may initially be unattached to the housing 702. Additionally, the hermetic sealing 714-720 is initially unapplied. With reference to FIG. 7, the posts 708 and 710 may be inserted into respective post holes 748 and 750 in the housing 702. The posts 708 and 710 are then electrically coupled to the wires 724 and 726 via the passages 728 and 730. When the posts 708 and 710 are electrically coupled to the wires 724 and 726, the posts 708 and 710 may be mechanically coupled or fastened to the housing 702 via the hermetic seals 716 and 720. For example, a melted glass or melted ceramic material may be applied to the posts 708 and 710. The melted glass or ceramic then cools and hardens to form the hermetic seals 716 and 720.

In some other examples, the posts 708 and 710 may be sealed in place prior to electrically coupling the posts 708 and 710 to the wires 724 and 726. In such an example application, the posts 708 and 710 may extend through the hermetic seats 716 and 720 to allow electrical coupling to the wires 724 and 726.

The magnets 742 and 744 may then be inserted into the respective slots 744 and 746. Alternatively, the magnets 742 and 744 may be inserted at any other time prior to installing the cover 712. The cavities 744 and 746 may also be filled with an encapsulation material after inserting the magnets 742 and 744 or after installing the cover 712.

After the magnets 742 and 744 and the posts 708 and 710 are inserted, the cover 712 may be affixed to the housing 702. If the cover 712 is a metal material, the cover 712 may be welded and/or brazed to the housing 702. When the cover 712 is affixed, the posts 708 and 710 are at least partially within holes in the cover 712. As a result, when a hermetic sealing material is applied to the holes containing the posts 708 and 710, the hermetic seals 714 and 718 will mechanically couple the posts 708 and 710 to the cover 712.

The wire 706 may be attached to the posts 708 and 716 at any time after the posts 708 and 710 have been installed into the housing 702. However, if the wire 706 is attached to the posts 708 and 710 after the posts 708 and 710 have been attached to the cover 712, the posts 708 and 710 may be more resistant to movement as a result of placing the tension on the wire 706 between the posts 708 and 710.

Figure 9:
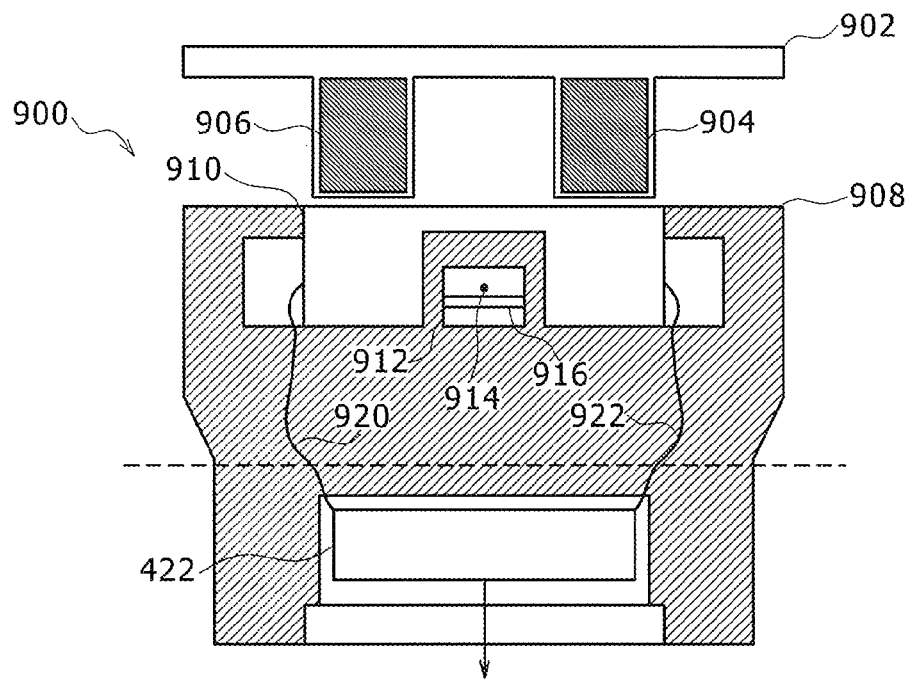
FIG. 9 is a cross-sectional view of an example vibrating wire viscometer with a cap including magnets.

FIG. 9 is a cross-sectional view of an example vibrating wire viscometer 900 with a cap 902 including magnets 904 and 906. The example vibrating wire viscometer 900 may be used to implement the example viscometer 60 described in connection with FIG. 3. As shown, the cap 902 is mechanically coupled to the magnets 904 and 906. The example cap 902 and the magnets 904 and 906 are installed simultaneously into a housing 908 by inserting the magnets 904 and 906 into a complementary-shaped cavity 910. The cap 902 is then fastened to the housing 908 by welding or brazing the cap 902 to the housing 908. The weld or braze seals the cavity 910 and the magnets 904 and 906 from exposure to downhole fluids that may damage the magnets 904 and 906.

The housing 908 further includes a flowline 912 to expose a vibrating wire 914 to the downhole fluid. The example flowline 912 runs parallel to the magnets 904 and 906 and, thus, the magnets 904 and 906 generate a magnetic field within the flowline 912 across the vibrating wire 914. The wire 914 is held within the flowline 912 by two posts 916 and 918. In the view illustrated in FIG. 9, the view of the post 918 is obscured by the post 916. The example posts 916 and 918 are each coupled to the electronics 422 via respective wires 920 and 922.

Figure 10:
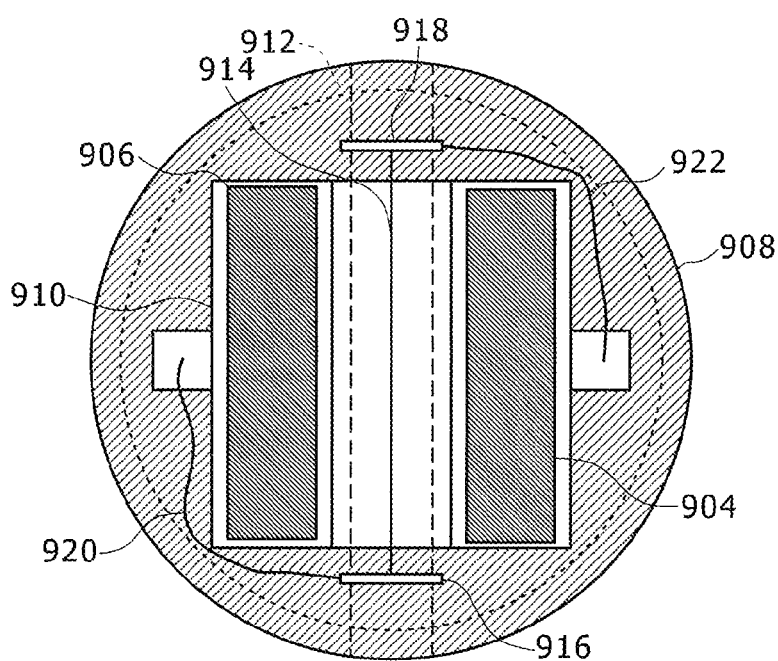
FIG. 10 is a plan view of the example vibrating wire viscometer of FIG. 9.

FIG. 10 is a plan view of the example vibrating wire viscometer of FIG. 9. The view illustrated in FIG. 10 shows example positioning and connections between the posts 916 and 918 and the wires 920 and 922. The example wires 920 and 922 may take any path(s) through the housing 908 from the electronic components 422 to the respective posts 916 and 918.

Figure 11:
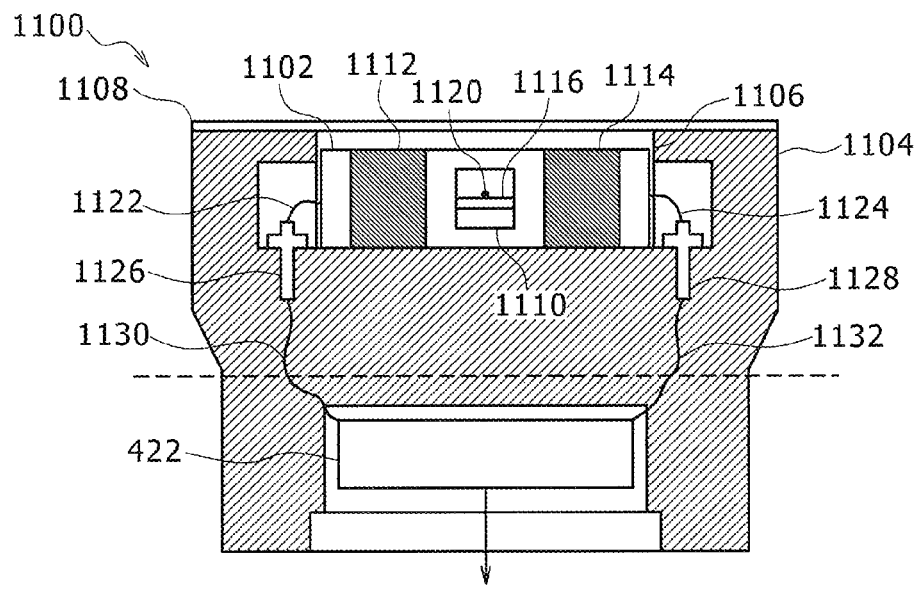
FIG. 11 is a cross-sectional view of an example vibrating wire viscometer including a removable sensor block.
Figure 12:
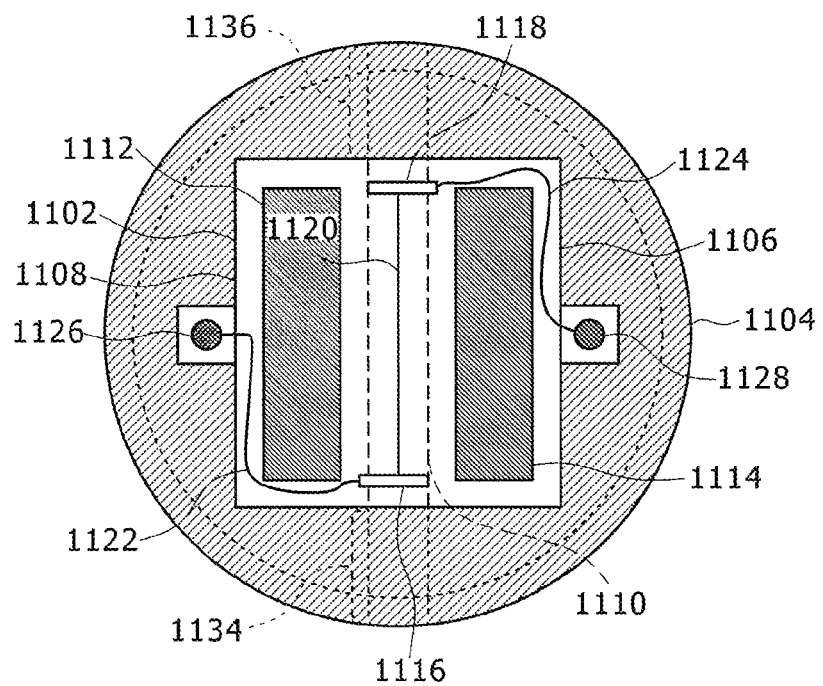
FIG. 12 is a top view of the example vibrating wire viscometer of FIG. 11.

FIG. 11 is a cross-sectional view of an example vibrating wire viscometer 1100 including a removable sensor block 1102. FIG. 12 is a plan view of the example vibrating wire viscometer 1100 of FIG. 11. The example vibrating wire viscometer 1100 may be used to implement the viscometer 60 described in connection with FIG. 3. A housing 1104 includes a slot or cavity 1106 into which the removable sensor block 1102 may be inserted. After inserting the removable sensor block 1102, a cover or cap 1108 may be affixed onto the housing 1104.

The example removable sensor block 1102 includes a flowline 1110, magnets 1112 and 1114, conductive posts 1116 and 1118, and a wire 1120. The conductive posts 1116 and 1118 hold the wire 1120 in tension within the flowline 1110 to immerse the wire 1110 in the downhole fluid. The wire 1120 may vibrate within the magnetic field generated by the magnets 1112 and 1114 when conducting an alternating current through the wire 1120. To provide the alternating current to the conductive posts 1116 and 1118 and the wire 1120, the removable sensor block 1102 further includes wires 1122 and 1124 electrically coupled to respective ones of the conductive posts 1116 and 1118. The example wires 1122 and 1124 are electrically and mechanically coupled to respective posts 1126 and 1128. The posts 1126 and 1128 are electrically coupled via respective wires 1130 and 1132 to the electronics 422.

The example housing 1104 also includes flowlines 1134 and 1136 shown in FIG. 12. The flowlines 1134 and 1136 are aligned with the flowline 1110 when the removable sensor block 1102 is inserted into the slot 1106. When the flowlines 1134, 1136, and 1110 are aligned, downhole fluid may freely flow around the wire 1120 and the conductive posts 1116 and 1118.

The example vibrating wire viscometer 1100 allows for easy removal and/or replacement of the sensor block 1102. For example, the removable sensor block 1102 may be configured to have a particular tension on the wire 1120 to vibrate within a particular resonant frequency range. The tension on the wire 1120 may be desirable for a range of expected downhole fluid viscosity, but may not be desirable for higher or lower viscosities outside the expected range. Therefore, another removable sensor block may also be configured to have a higher or lower wire tension than the wire 1120. To quickly change the wire tension in the vibrating wire viscometer 1100, the sensor block 1102 is removed by unfastening the wires 1122 and 1124 from the posts 1126 and 1128 and removing the sensor block 1102 from the slot 1106. Another removable sensor block is then inserted into the slot 1106 and the respective wires are fastened to the posts 1126 and 1128. The cover 1108 may then be attached or re-attached to the housing 1104.

Figure 13:
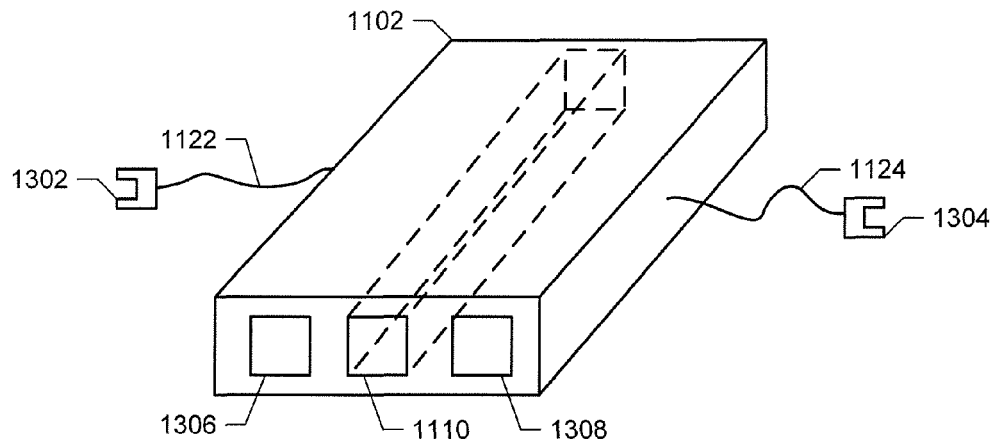
FIG. 13 is an isometric view of the example removable sensor block of FIG. 11.

FIG. 13 is an isometric view of the example removable sensor block 1102 of FIG. 11. As mentioned above, the removable sensor block 1102 includes the wires 1122 and 1124 to electrically couple the conductive posts 1116 and 1118 to the electronics 422. The wires 1122 and 1124 may also include connectors 1302 and 1304 to mechanically couple the wires 1122 and 1124 to the posts 1126 and 1128.

The flowline 1110 extends along the length of the removable sensor block 1102. However, the example magnets 1112 and 1114 may be inserted into the removable sensor block 1102 via, for example, slots or cavities 1306 and 1308 that do not extend along the entire length of the removable sensor block 1102. In some other examples, the cavities 1306 and 1308 extend along the entire length of the removable sensor block 1102 to facilitate insertion and removal of the magnets 1112 and 1114. In some examples, either or both ends of the cavities 1306 and 1308 are plugged to prevent the magnets 1112 and 1114 from falling out.

Figure 14:
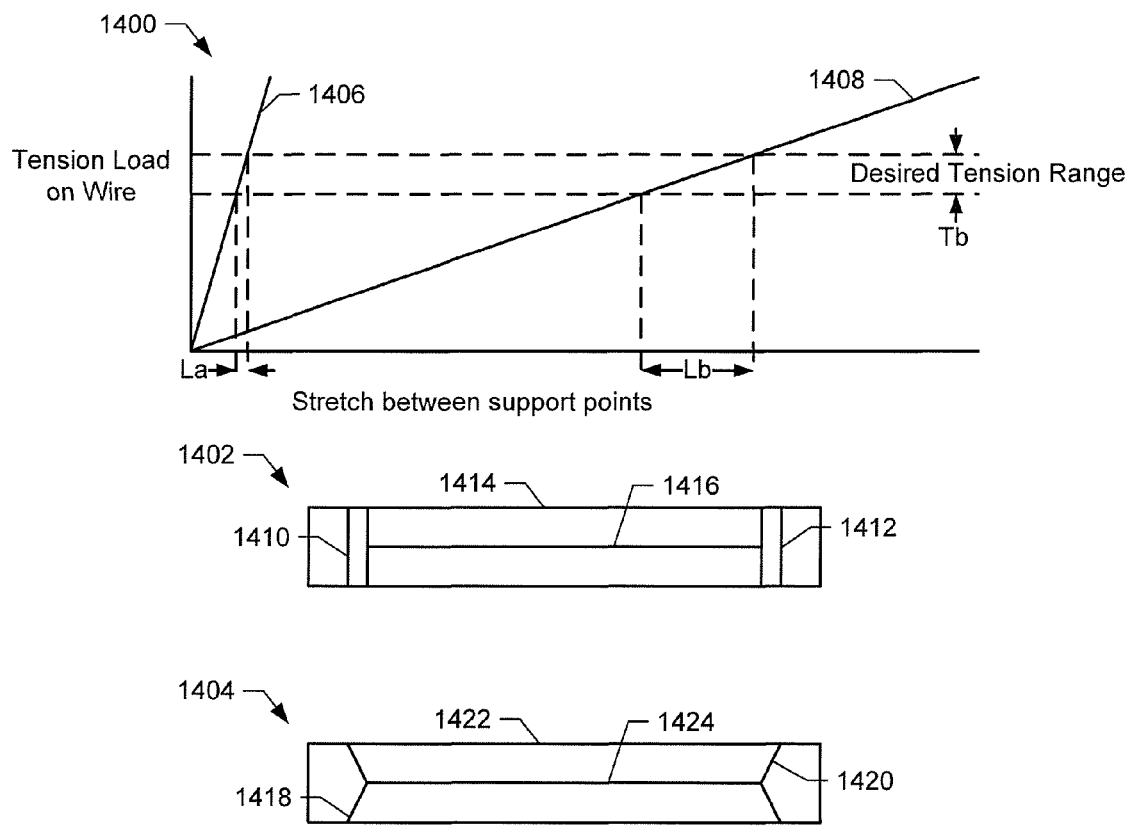
FIG. 14 is a graph illustrating the wire tension and post stretch relationships between two illustrated wire and post configurations.

FIG. 14 is a graph 1400 illustrating the wire tension and wire stretch relationships between two illustrated wire and post configurations 1402 and 1404. As mentioned above, the tension on the wire portion of a vibrating wire viscometer affects the resonant frequency of the vibrations. If the tension is too low, the frequency may be too low. Similarly, if the tension is too high, the frequency may be too high. A desired frequency range is often established to optimize or adjust the signal strength to match the frequency response capabilities of a signal analyzer.

The example graph 1400 of FIG. 14 illustrates two wire tension and wire stretch relationships or curves 1406 and 1408. The example curve 1406 illustrates the wire tension and wire stretch relationship for the example wire and post configuration 1402. The example curve 1408 illustrates the wire tension and wire stretch relationship for the example wire and post configuration 1404.

The wire and post configuration 1402 includes two posts 1410 and 1412 mechanically coupled to a flowline 1414. The posts 1410 and 1412 hold a wire 1416 in tension. The posts 1410 and 1412 are rigidly fastened to the sides of the flowline 1414. Thus, any stretch between the posts 1410 and 1412 is caused almost completely by stretching the wire 1416. In contrast, the wire and post configuration 1404 includes two posts 1418 and 1420 mechanically coupled to a flowline 1422. The posts 1418 and 1420 hold a wire 1424 in tension. Unlike the posts 1410 and 1412, the posts 1418 and 1420 may flex in response to tension on the wire 1424 to increase or decrease stretch between support points. The flex of the posts 1418 and 1420 may be adjusted by changing the thickness (e.g., diameter) of the posts 1418 and 1420 and/or using different materials. In some examples such as those illustrated in FIGS. 17E and 17F, the posts 1418 and/or 1420 may be cantilevered posts to flex in response to tension on the wire 1424. Each unit of additional stretch between the support points on the wire 1424 and the posts 1418 and 1420 causes less tension on the wire 1424 than the stretch on the wire 1416, and the desired tension range on the wire 1424 is easier to achieve because the range of stretch is much larger. This is particularly important when the flowline 1422 and the posts 1418 and 1420 expand due to downhole temperature and pressure conditions.

The respective slopes of the lines 1406 and 1408 are based on the flexibility of the posts 1410, 1412, 1418, and 1420. The posts 1410, 1412, 1418, and 1420 may be made more or less flexible to accommodate different lengths of wire and/or different sizes of a vibrating wire viscometer tool. Smaller tools may use more rigid posts such as the posts 1410 and 1412. In contrast, tools with more room to stretch may use the posts 1418 and 1420 to more easily achieve the desired tension range.

Figure 15:
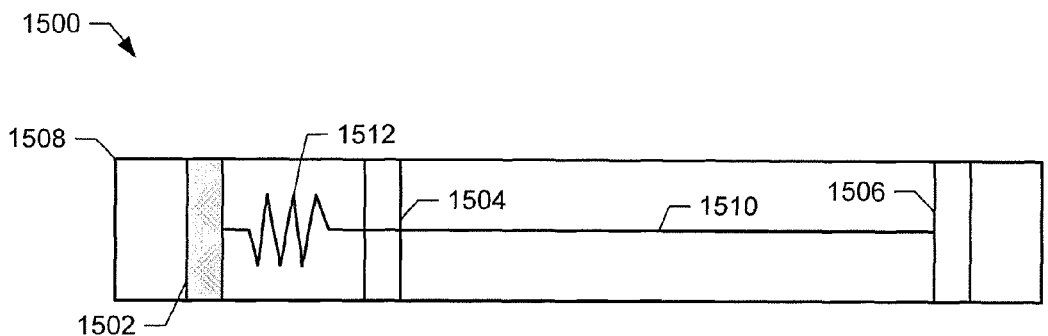
FIG. 15 is a schematic diagram of an example wire and post configuration to maintain wire tension.

FIG. 15 is a schematic diagram of an example wire and post configuration 1500 to maintain wire tension. The example configuration 1500 may be used in any of the example vibrating wire viscometers illustrated and described in connection with FIGS. 4-12 above. The example wire and post configuration 1500 includes posts 1502, 1504, and 1506. The posts 1502-1506 are mechanically coupled to a flowline 1508, through which downhole fluid may flow during a sampling operation to immerse a vibrating wire 1510. The example posts 1504 and 1506 are conductive and may deliver an alternating current to the wire 1510 to cause the wire 1510 to vibrate at a desired frequency in the presence of a magnetic field.

The wire 1510 is further coupled to the post 1502 via a spring 1512. The example post 1502 may be non-conductive to prevent stray currents or short circuits. The spring 1512 places the wire 1510 under a substantially constant tension to maintain the resonant frequency within a desired range. The spring 1512 may be configured to place tension on the wire 1510 and hold the wire against the post 1504. The wire 1504 then vibrates between the posts 1504 and 1506 but does not vibrate the spring 1512.

Figure 16:
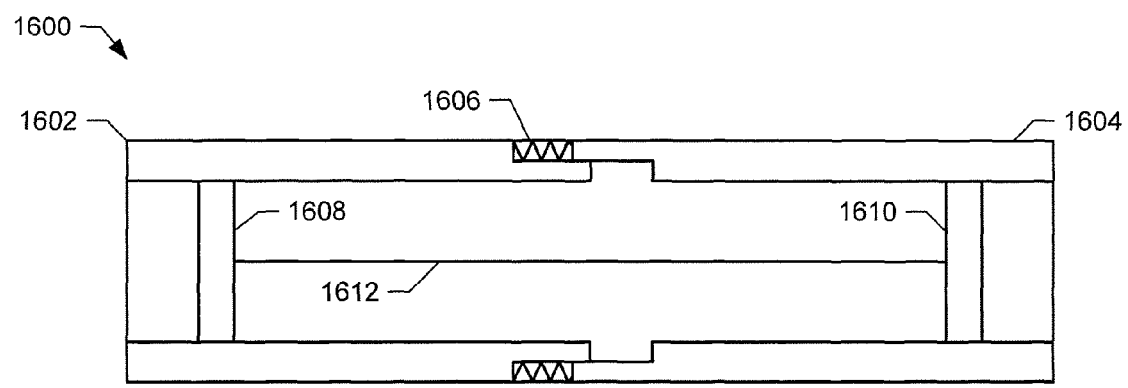
FIG. 16 is a schematic diagram of an example wire, post and flowline configuration to maintain wire tension.

FIG. 16 is a schematic diagram of an example wire, post, and flowline configuration 1600 to maintain a desired wire tension. The example configuration 1600, like the configuration 1500 described in connection with FIG. 15, may be used in any of the example vibrating wire viscometers illustrated and described in connection with FIGS. 4-12 above.

The example wire, post, and flowline configuration 1600 includes two flowline tubes 1602 and 1604. A spring 1606 pushes the flowline tubes 1602 and 1604 apart. A first post 1608 is mechanically coupled to the first flowline tube 1602 and a second post 1610 is mechanically coupled to the second flowline tube 1604. Either or both of the posts 1608 and 1610 may also be electrically coupled to the respective tubes 1602 and/or 1604. The posts 1608 and 1610 hold a wire 1612 in tension and may conduct an alternating current through the wire 1612 to cause the wire 1612 to vibrate in the presence of a magnetic field.

The spring 1606 urges the flowline tubes 1602 and 1604 apart, while the wire 1612 and the posts 1608 and 1610 hold the tubes 1602 and 1604 together. Thus, the force exerted on the tubes 1602 and 1604 by the spring 1606 is directly opposed by the tension force on the wire 1612. The spring 1606 may therefore be used to control the tension on the wire 1612 and maintain the vibration frequency within a desired frequency range. A spring 1606 having a higher spring force or constant may keep a higher tension on the wire 1612. In contrast, configuring the spring 1606 to have a lower spring force or spring constant may allow a lower tension on the wire 1612.

FIGS. 17A-17F illustrate example wire, post, and flowline configurations 1702, 1704, 1706, 1708, 1742, and 1744 to electrically decouple a vibrating wire and supporting posts from a flowline. The example configurations 1702, 1704, 1706, 1708, 1742, and 1744 may be implemented in any of the example vibrating wire viscometers illustrated and described in FIGS. 4-12.

Figure 17A:
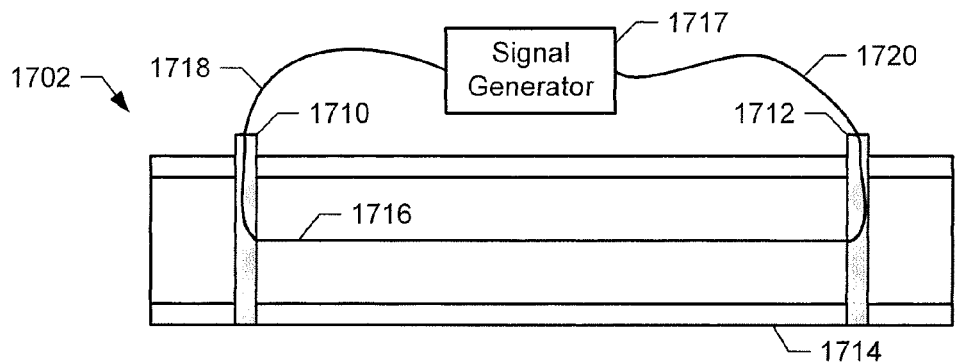
FIGS. 17A-17F illustrate example wire, post and flowline configurations to supply an alternating current to a wire.

FIG. 17A illustrates the example configuration 1702 utilizing electrically non-conductive posts 1710 and 1712. The non-conductive posts 1710 and 1712 may be directly attached to a conductive flowline 1714. A vibrating wire 1716 may then be fastened between the non-conductive posts 1710 and 1712. To couple the wire 1716 to a signal generator 1717 to receive an alternating current, lead wires 1718 and 1720 may be coupled to the vibrating wire 1716. In some examples, the lead wires 1718 and 1720 are run through the non-conductive posts 1710 and 1712 from the vibrating wire 1716 outside the flowline 1714.

Figure 17B:
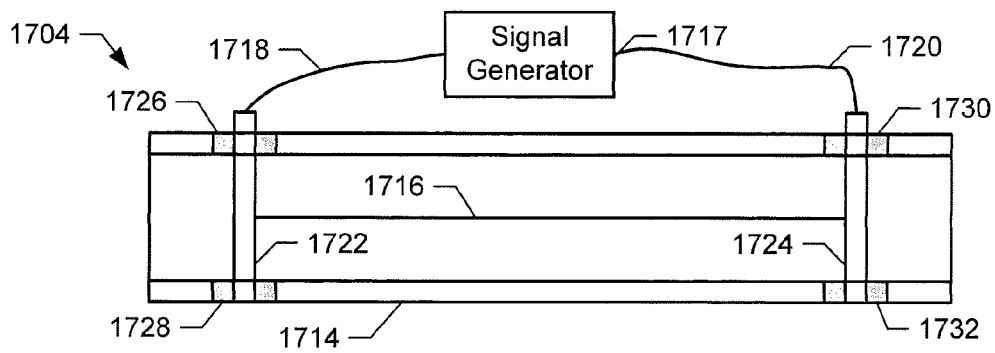

FIG. 17B illustrates another example configuration 1704 utilizing electrically conductive posts 1722 and 1724 electrically decoupled or insulated from an electrically conductive flowline 1714 via non-conductive connectors 1726, 1728, 1730, and 1732. The wire 1716 is fastened to the conductive posts 1722 and 1724, which are electrically coupled to a signal generator 1717 via the wires 1718 and 1720 to deliver an alternating current to the wire 1716.

Figure 17C:
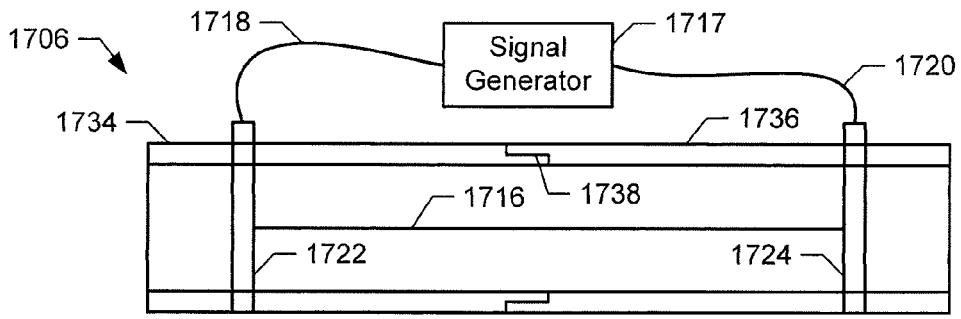

FIG. 17C illustrates yet another example configuration 1706 utilizing separate conductive tubes 1734 and 1736 that are mechanically coupled. The tubes 1734 and 1736 are also electrically decoupled or insulated from each other by a non-conductive substance 1738 that may be applied to any areas where the tubes 1734 and 1736 would otherwise make mechanical and/or electrical contact. The electrically conductive posts 1722 and 1724 are then mechanically and electrically coupled to respective ones of the tubes 1734 and 1736. The wire 1716 is fastened in tension to the posts 1722 and 1724. An alternating current may then be applied to the wire 1716 via the posts 1722 and 1724 and/or the tubes 1734 and 1736 to cause the wire 1716 to vibrate at a resonant frequency in the presence of a magnetic field. To deliver the alternating current, the posts 1722 and 1724 and/or the tubes 1734 and 1736 may be electrically coupled to a signal generator 1717 via the wires 1718 and 1720.

Figure 17D:
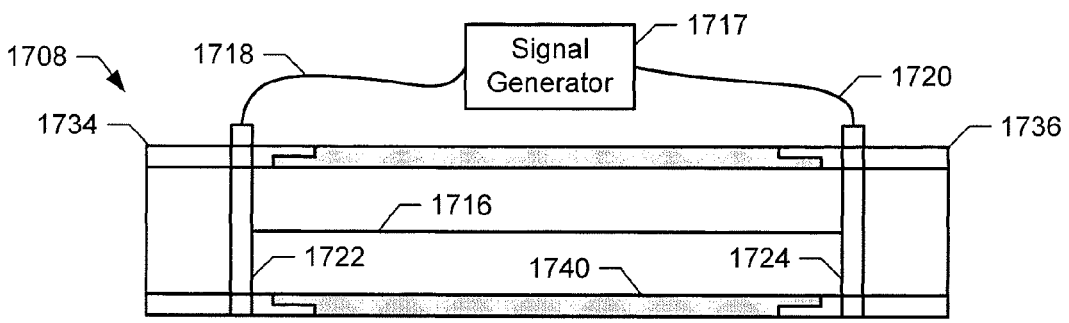

FIG. 17D illustrates another configuration 1708 including an electrically non-conductive tube 1740 mechanically coupled to the electrically conductive tubes 1734 and 1736. The conductive tubes 1734 and 1736 and the non-conductive tube 1740 may cooperate to provide a flowline. The electrically conductive posts 1722 and 1724 are mechanically and electrically coupled to the respective conductive tubes 1734 and 1736 to hold the wire 1716 in tension between the posts 1722 and 1724. An alternating current may then be applied to the wire 1716 via the posts 1722 and 1724 and/or the tubes 1734 and 1736 to cause the wire 1716 to vibrate at a resonant frequency in the presence of a magnetic field. The signal generator 1717 may supply the alternating current to the wire 1716 via the wires 1718 and 1720, which are electrically coupled to the posts 1722 and 1724 and/or the conductive tubes 1734 and 1736. The non-conductive tube 1740 prevents a short circuit from bypassing the wire 1716 through the conductive tubes 1734 and 1736.

Figure 17E:
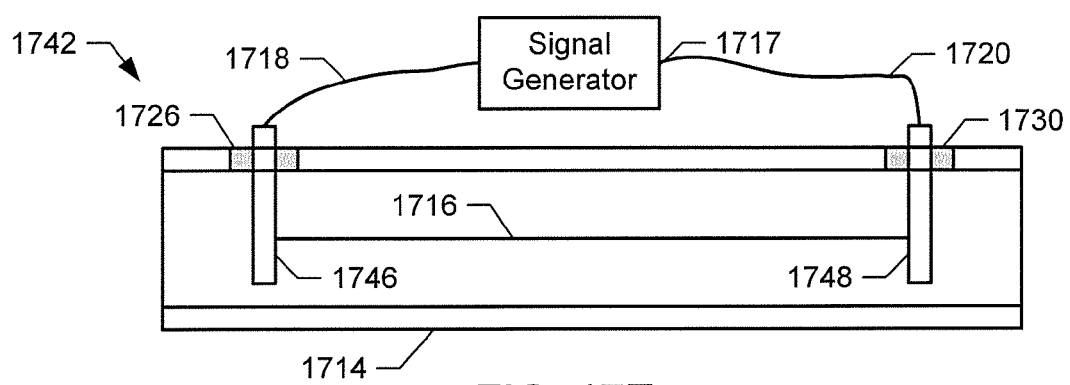

FIG. 17E illustrates another example configuration 1742 including electrically conductive cantilevered posts 1746 and

1748. The cantilevered posts 1746 and 1748 are each attached at a respective point on the flowline 1714 via non-conductive seals 1726 and 1730. The vibrating wire 1716 is held in tension between the posts 1746 and 1748. By attaching each of the cantilevered posts 1746 and 1748 at one point instead of multiple points, the posts 1746 and 1748 are more flexible and maintain a more consistent tension on the vibrating wire 1716 as described in connection with FIG. 14 above. The example posts 1746 and 1748 are electrically coupled to the signal generator 1717 via the wires 1718 and 1720 to deliver a current to the vibrating wire 1716. Additionally, the example posts 1746 and 1748 are mechanically coupled to the same side of the flowline 1714, and therefore the wires 1718 and 1720 may be passed through one slot instead of two slots (e.g., the slots 408 and 410 of FIG. 4).

Figure 17F:
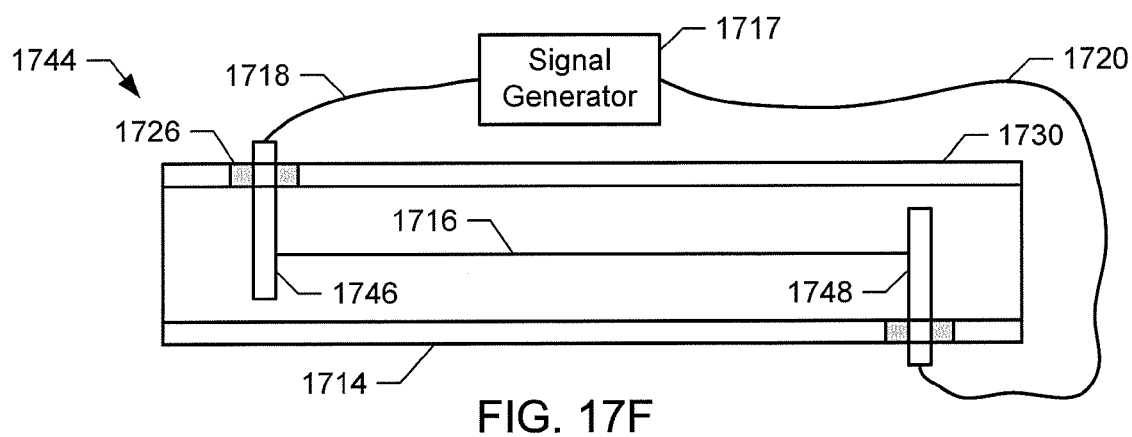

FIG. 17F also illustrates an example configuration 1744 including the electrically conductive cantilevered posts 1746 and 1748. In contrast to the example configuration 1742 of FIG. 17E, the cantilevered posts 1746 and 1748 of FIG. 17F are mechanically coupled to opposite sides of the flowline 1714. The wires 1718 and 1720 may then be passed through two slots (e.g., the slots 408 and 410 of FIG. 4) instead of the same slot.

FIG. 18 is a schematic diagram of an example vibrating wire viscometer 1800 configuration including electromagnets 1802 and 1804. The example electromagnets 1802 and 1804 generate a magnetic field across a vibrating wire 1806 within a flowline 1808. The example electromagnet 1802 is implemented using a wire 1810 coiled around a high-permeability magnetic core 1812. Similarly, the electromagnet 1804 is implemented using a wire 1814 coiled around a high-permeability magnetic core 1816. The magnetic cores 1812 and 1816 may be implemented using, for example, a ferrite material.

The example wires 1810 and 1814 are wrapped around the respective cores 1812 and 1816 in the same direction to generate a magnetic field having the same direction. To generate a magnetic field, an alternating current is applied to the wires 1810 and 1814 by a signal generator 1818. The wire 1810 is electrically coupled to the signal generator 1818 via wires 1820 and 1822. Similarly, the wire 1814 is electrically coupled to the signal generator 1818 via wires 1824 and 1826. The wires 1820-1826 deliver the alternating current from the signal generator 1818 to the wires 1810 and 1814.

When an alternating current is applied, the electromagnets 1802 and 1804 generate a magnetic field perpendicular to the wire 1808. When a current is applied to the wire 1808, the wire 1808 vibrates. The magnitude of the vibration is proportional to the strength of the magnetic field and the current flowing through the wire 1808. By increasing the current to the electromagnets 1802 and 1804, the magnetic field strength increases and increases the magnitude of the vibration. As a result, the electromagnets 1802 and 1804 may be useful to accurately measure the viscosities of different types of fluids.

Figure 19:
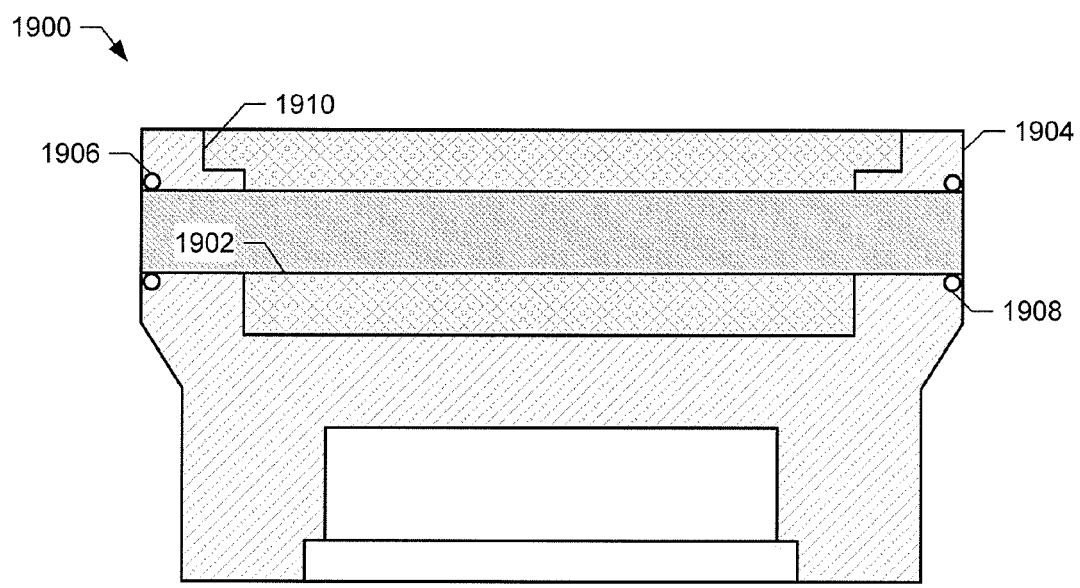
FIG. 19 is a schematic diagram of an example vibrating wire viscometer configuration including a removable flowline.

FIG. 19 is a schematic diagram of an example vibrating wire viscometer configuration 1900 including a removable flowline 1902. The example viscometer configuration 1900 may be used to implement the viscometer 60 illustrated in FIG. 3. The example flowline 1902 may be implemented using any of the example flowline configurations 1702, 1704, 1706, 1708, 1742, and/or 1744 illustrated in FIGS. 17A-17F. The flowline 1902 is inserted into a housing 1904 and seals 1906 and 1908 are applied. The seals 1906 and 1908 prevent downhole fluid from accessing components within the housing 1904. The example seals 1906 and 1908 may be implemented by, for example, welding, brazing, and/or using elastomer seals. By inserting a separate flowline 1902 into the housing 1904, the viscometer configuration 1900 may be rapidly assembled, and different flowlines 1902 may be quickly swapped to increase sampling and testing speed. Flowlines 1902 may differ in materials, construction (e.g., conductive paths), and/or size.

The housing 1904 farther includes one or more slots or chambers 1910. The example slots 1910 may hold, for example, magnets, electromagnets, wiring, and/or other components to implement a vibrating wire viscometer as described herein. Additionally, the example slot(s) 1910 may be filled with an encapsulation material such as the material described in connection with FIGS. 4-6 above. The encapsulation material protects the components in the slot(s) 1910.

Although example methods, apparatus and articles of manufacture have been described herein, the scope of coverage of this patent is not limited thereto. On the contrary, this patent covers every apparatus, method and article of manufacture fairly falling within the scope of the appended claims either literally or under the doctrine of equivalents.

What is claimed is:

1. A vibrating wire viscometer housing, comprising:
   a flowline through the housing to expose a first wire to a downhole fluid;
   a cavity in the housing to hold a magnet and to conduct one or more additional wires from the flowline to a signal generator;
   first and second electrically conductive posts mechanically coupled to the housing to hold the first wire in tension within the flowline; wherein the conductive posts are electrically insulated from the housing and extending from the cavity to the flowline;
   an analyzer electrically coupled to the first and second electrically conductive posts via at least the cavity to determine a viscosity based on the vibration of the electrically conductive wire; and
   a seal mechanically coupled to the housing to prevent access to the magnet by the downhole fluid.

2. The vibrating wire viscometer housing as defined in claim 1, wherein the first wire is to vibrate in response to an alternating electrical current delivered to the first wire via the conductive posts.

3. The vibrating wire viscometer housing as defined in claim 2, further comprising a signal generator to generate the alternating electrical current and electrically coupled to the first wire via the first and second conductive posts.

4. The vibrating wire viscometer housing as defined in claim 1, wherein the seal comprises an encapsulation material in the cavity to prevent contact between the one or more additional wires, the magnet, or the signal generator and the downhole fluid.

5. The vibrating wire viscometer housing as defined in claim 4, wherein the encapsulation material applies a first fluid pressure from the downhole fluid to the flowline to balance a second fluid pressure from the downhole fluid in the flowline.

6. The vibrating wire viscometer housing as defined in claim 1, further comprising a second cavity to hold a second magnet.

7. The vibrating wire viscometer housing as defined in claim 6, wherein the seal comprises an encapsulation material to prevent contact between the first and second magnets or a signal generator and the downhole fluid.

8. The vibrating wire viscometer housing as defined in claim 7, wherein the seal further comprises a flexible cover to prevent contact between the downhole fluid and the encapsulation material and to apply fluid pressure to the encapsulation material from the downhole fluid.

9. The vibrating wire viscometer housing as defined in claim 6, further comprising first and second holes extending between the first and second cavities through the flowline to hold the first and second conductive posts.

10. The vibrating wire viscometer housing as defined in claim 1, wherein the first conductive post flexes in response to an increased tension on the first wire.

11. The vibrating wire viscometer housing as defined in claim 1, wherein the first conductive post is fastened to at least one of the housing or the flowline at a plurality of points.

12. The vibrating wire viscometer housing as defined in claim 1, wherein the flowline comprises first and second electrically conductive tubes that are mechanically coupled and electrically insulated from each other.

13. The vibrating wire viscometer housing as defined in claim 12, wherein the first and second electrically conductive tubes are mechanically coupled via a spring to apply a substantially constant tension to the first wire.

14. The vibrating wire viscometer housing as defined in claim 12, wherein the first and second electrically conductive tubes are mechanically coupled and electrically insulated from each other via an electrically non-conductive tube.

15. The vibrating wire viscometer housing as defined in claim 1, wherein the magnet comprises an electromagnet.

16. The vibrating wire viscometer housing as defined in claim 1, wherein the first conductive post is a cantilevered post.

17. The vibrating wire viscometer as defined in claim 15, wherein the housing further comprises first and second fasteners to mechanically fasten the first and second signal wires to the housing.

18. The vibrating wire viscometer, comprising:
a metallic housing comprising a cavity and a flowline fluidly decoupled from the cavity;
first and second electrically conductive posts electrically insulated from the metallic housing and extending from the cavity to the flowline;
an electrically conductive wire held in tension between the first and second electrically conductive posts to vibrate in response to an electrical signal;
a magnet in the cavity and extending parallel to the conductive wire;
an analyzer electrically coupled to the first and second electrically conductive posts via at least the cavity to determine a viscosity based on the vibration of the electrically conductive wire; and
an encapsulation material to fill the cavity to fluidly decouple the cavity from the flowline and from a downhole fluid surrounding the metallic housing.

* * * * *